United States Patent [19]

Nolan et al.

[11] Patent Number: 5,070,012
[45] Date of Patent: Dec. 3, 1991

[54] MONITORING OF CELLS AND TRANS-ACTIVATING TRANSCRIPTION ELEMENTS

[75] Inventors: Garry P. Nolan, Granby, Conn.; Steven Fiering, Palo Alto; Leonard A. Herzenberg, Stanford, both of Calif.

[73] Assignee: The Board of Trustees of the Leland Stanford Junior University, Stanford, Calif.

[21] Appl. No.: 175,416

[22] Filed: Mar. 30, 1988

[51] Int. Cl.$^5$ ............................................. C12Q 1/68
[52] U.S. Cl. ............................................ 435/6; 435/5; 435/8; 435/14; 435/18; 435/34
[58] Field of Search ................... 435/6, 5, 8, 14, 18, 435/34

[56] References Cited

U.S. PATENT DOCUMENTS

| | | | |
|---|---|---|---|
| 4,499,183 | 2/1985 | Sujansky | 435/6 |
| 4,607,008 | 8/1986 | Coates | 435/5 |
| 4,661,443 | 4/1987 | Brot | 435/6 |
| 4,743,535 | 5/1988 | Carrico | 435/6 |
| 4,861,709 | 8/1989 | Ulitzur | 435/5 |

OTHER PUBLICATIONS

Jongkind, J. F., "Detection of Acid β-Galactosidase . . . ", Cytometry 7(5), 1986, 463–466.
Srienc, F., "Flow Cytometry Analysis of Recombinant . . . ", Cytometry 7(2), 1986, 132–141.
Konijn, A. M., "A Rapid & Sensitive Enzyme Linked Immuno-Sorbent Assay", J. Immunol. Methods 54(3), 1982, 297–308.

*Primary Examiner*—Robert A. Wax
*Assistant Examiner*—Frederick F. Isung
*Attorney, Agent, or Firm*—Bertram I. Rowland

[57] ABSTRACT

Methods and compositions are provided for analyzing in viable cells gene expression regulatory elements and systems. The method can be used to evaluate a transcriptional initiation regulatory system or the presence of a trans acting component. The method finds use in evaluating various transcriptional initiation functional sequences for use in expression of products, for the detection of trans acting agents associated with viruses and for quantitating the presence of infectious viruses. The method comprises introducing an expression cassette encoding an enzyme which has a fluorescent substrate, substantially irreversibly introducing the substrate into the cell host and detecting the formation of fluorescence during a predetermined time interval.

13 Claims, No Drawings

MONITORING OF CELLS AND TRANS-ACTIVATING TRANSCRIPTION ELEMENTS

INTRODUCTION

1. Technical Field

The field of this invention concerns identifying cells and levels of expression employing in vitro prepared expression constructs.

2. Background

There are many situations where one wishes to differentiate cells by virtue of a particular phenotype or genotype. There may be an interest in the efficiency of transfection or transformation. Alternatively, there may be an interest in the efficiency of a particular promoter or enhancer or other transcriptional regulatory element, either by itself or in combination with other regulatory elements. The regulatory elements may be endogenous to the cell or may be as a result of the presence of a virus. In some situations it may be desirable to determine the presence of a virus or virus particle in a physiological fluid or cell, either qualitatively or quantitatively.

Various techniques have been reported for determining virus titer. For example, retroviruses may be detected by exposing host cells to cells or medium suspected of containing the retrovirus and waiting for sufficient time, frequently many days, before assaying for reverse transcriptase. This method is inconvenient and it is difficult to provide a quantitative or semi-quantitative determination of the number of virus particles.

There is, therefore, substantial need and interest in being able to evaluate various aspects of transcription and expression, in determining cellular processes, the presence of pathogens, such as viruses, or the like.

3. Relevant Literature

LacZ has found effective use as a marker for genetic tagging. Sanes et al., *EMBO J.* (1986) 5:3133-3142 and Price et al., *Proc. Natl. Acad. Sci. U.S.A.* (1987) 84:156-160. Fluorescence activated cell sorting has proven invaluable in the analysis and viable sorting of complex cell populations. Parks et al., (1986) *The Handbook of Experimental Immunology*, 4th edition, eds. Weir et al. (Blackwell Scientific Pub., Ltd., Edinburgh) Chapter 29, pp. 29.1-29.21. Attempts to quantitate single, viable eukaryotic cells have either failed or led to dead cells. MacGregor et al., *Somat. Cell and Molec. Gen.* (1987) 13:253-265; Srienc et al., *Cytometry* (1986) 7:132-141.

Fluorescein passes the cell membrane over 200 times faster at 37° C. than 5° C., while the $V_{max}$ of $\beta$-galactosidase is lowered by only ten-fold over this temperature differential. Thomas et al., *Biochemistry* (1979) 18:2210-2218; Wallenfels and Melhotra (1960) in *The Enzymes*, 2nd edition, eds. Boyer et al. (Academic Press, N.Y.).

SUMMARY OF THE INVENTION

Transcriptional events in a viable mammalian host cell can be monitored by introducing into the host cell an expression construct comprising a transcriptional initiation regulatory region associated with a gene which transforms a substrate to a fluorescent product. The substrate is characterized by being capable of being transported across the cellular membrane under a first set of conditions, and will be maintained within the cell under a second set of conditions, where the fluorescent product will be maintained in the cell under the second set of conditions. Desirably, a competitive and cell permeable enzyme inhibitor is employed which can be used to modulate the observed enzyme activity or substrate turnover. The method finds wide use in evaluating transfection, transcription, and detecting infectious viral particles.

DESCRIPTION OF SPECIFIC EMBODIMENTS

Methods and compositions are provided for producing a fluorescent product in a mammalian host cell, where the fluorescent product may be related to a wide variety of events of interest. The method involves employing a construct having a selected transcriptional initiation region related to the information to be determined, which regulates the transcription of a structural gene encoding an enzyme. The enzyme has a substrate which is characterized by being capable of being transported across the cellular membrane under a first set of conditions and being retained within the cell under a second set of conditions, which conditions also provide for the retention of the product within the cell. The enzyme product will be fluorescent and the level of fluorescence of the cell may be detected in a variety of ways. In addition, it is desirable that the enzyme which is selected either has a low or no background level in the cellular host or the endogenous enzyme may be selectively inhibited relative to the introduced enzyme. In addition, it is desirable that the enzyme activity or turnover rate may be modulated by employing a competitive inhibitor, so that a substantially extended dynamic range of enzyme activity can be addressed.

An enzyme which has found extensive use and fulfills the desired characteristics is $\beta$-galactosidase. The enzyme is characterized as having a broad specificity so as to accommodate the use of different analogs as substrates and inhibitors, a high turnover rate and being very stable. In addition, the galactosidyl group can be used as an etherifying group, particularly with fluorescent phenolic compounds to change the fluorescence characteristics, so that the unetherified product may be excited at a wavelength, which does not excite the etherified product. $\beta$-Galactosidase will be used as paradigmatic of enzymes generally and $\beta$-galactosidyl substituted fluoresceins or substituted derivatives thereof will be paradigmatic of substrates, for not only $\beta$-galactosidase, but such other enzymes which may find use. There are various recombinant forms of $\beta$-galactosidase, where the $\beta$-galactosidase may be associated with the nuclear membrane or the cytosol. Of particular interest is bacterial $\beta$-galactosidase, more particularly, *E. coli* $\beta$-galactosidase.

For the most part, the enzymes alternative to $\beta$-galactosidase, will be hydrolases or oxidoreductases. By selecting for enzymes coming within these groups, which enzymes have the characteristics described for $\beta$-galactosidase and whose substrates have the characteristics described for $\beta$-galactosidyl fluorescein, one may select other enzymes and substrates. Other enzymes include saccharidases, such as $\beta$-glucosidase, $\beta$-glucuronidase, $\alpha$-galactosidase, $\beta$-hexosaminidase, etc., luciferase, Tetrahymena self-splicing RNA, esterases, such as cholesterol esterase, arylsulfatase, phospholipase, phosphatase, etc.

The expression construct will be comprised of the transcriptional initiation regulatory region, the gene encoding the enzyme of interest, particularly $\beta$-galactosidase, and a transcriptional termination region. For the most part, the elements of the transcriptional initiation regulatory region will be modified in accordance with the questions asked when investigating a particular system. For example, the construct may be employed in determining the efficiency of infection where infection includes recombinant or defective retrovirus or similar virus infection: Epstein-Barr virus derived virus constructs leading to episomal maintenance: and transformation, where transformation includes transfection, transduction, or transformation employing various agents, such as electroporation, permeabilizing the membrane, for example with calcium phosphate, lysozyme, etc., or the like. Thus, a procedure is provided where the particular target host or DNA introduction procedure may be evaluated by the subject method by comparing the fluorescence of the various cells which receive the DNA under different conditions.

The construct may also be used to evaluate the presence and efficiency of various functional transcriptional initiation regulatory regions or elements in a particular mammalian cell host. For example, the enhancer and promoter of immunoglobulin expression may be employed to determine the efficiency of transcription in lymphocytes, myeloid cells, hematopoietic cells, or other cells. Alternatively, one may be interested in trans acting agents, which provide for repression or activation of transcription. Thus, one may screen, with the construct, a wide variety of cells for such trans acting agent by selection of the appropriate transcriptional initiation regulatory region. For example, one may use the subject method to screen for regions associated with interferon induction of MHC expression, transduction of signals by ligands, regulation of enhancers, cloning of trans acting regulatory proteins, etc. Alternatively, one can screen for regions associated with enhancement or repression, by putting various DNA fragments in the construct and detecting the amount of fluorescence produced in the host cell.

Of particular interest is the determination, particularly quantitative determination, of functional virus particles in a physiological medium or cells from a mammalian host. For this purpose, a host cell is selected which is susceptible to infection by the virus. As an illustration, to screen for HIV, cells such as Jurkat and Molt-4 human T-cells, H9 human T-cell line, CD4+ cells, macrophages, and endothelial cells, either wild type or transformed, may be employed. (As another example, for hepatitis virus, hepatic cells may be employed.) The expression construct is introduced into these cells with the LTR (long terminal repeat) of HIV, thus creating a target "test" cell line. It is known that the tat (trans activating transcription) gene product greatly enhances, by a factor of $10^2$ or greater, the expression of the viral genes. By co-culturing the host cell containing the expression construct with the physiological fluid to be screened for the presence of viral particles or with potentially infected cells to determine whether the cells are infected with infectious viral particles, the host target cells become infected with the infectious agent. Thus, one can then co-cultivate the host cells with either the serum or dispersed isolated cells from the individual being screened. Co-cultivation can be carried out by any convenient means. See for example, Sarres et al., *EMBO J.* (1986) 5:3133-3142: Keller et al., *Nature* (1985) 318:149-154.

In order to quantitatively assay for the enzyme activity in the host cells, the substrate should be transferred into the cell in an amount in substantial excess of the amount of enzyme, as well as substantially greater than $K_m$, preferably at least about two-fold greater than $K_m$. The significant factor is that based on the enzyme activity, one can obtain a rate which is substantially linear, that is, the observed rate is at enzyme saturation. With $\beta$-galactosidase, this can be readily achieved with fluorescein derivatives, particularly fluorescein dibetagalactosidase, more particularly anionic substituted fluoresceins, such as carboxyfluorescein, phosphonylfluorescein, sulfonylfluorescein, etc. Other fluorogenic substrates include fluorescein diacetate, 4-methylumbelliferyl acetate or $\beta$-galactoside, fluorescent nucleotides, for example trinitrophenyladenosine-5'-triphosphate.

The fluorogenic compounds may be introduced into the cells employing first conditions, namely a hypotonic solution at a temperature in the range of about 25° to 40° C., preferably about 37° C. By employing a low osmolality medium, usually at least about 25% lower than isotonic and usually not more than about 10-fold lower than isotonic, for a short time, generally from about 10 sec to 5 min, the cells swell and the fluid entering the cells carries with it small molecules such as fluorogenic substrates. Thus, a relatively high concentration of substrate within the cells can be achieved in this manner. Usually the concentration of substrate in the external medium will be at least about 100 $\mu$M to 2 mM, limited by such considerations as the solubility of the substrate. Various other techniques may be employed as first conditions to provide for the osmotic shock of the cells, for example an initial treatment with glycerol followed by substrate containing medium. Frost and Williams, *Virology* (1978) 91:39-50.

Other methods for introducing the enzyme substrate into the cells include passive diffusion of substrate, where the enzyme produces a change in the substrate giving a product which, because of increased polarity or a revealed reactive group which becomes bound to a cellular constituent, remains in the cell: and active transport of substrate into the cells by taking advantage of a cellular transport process. Substrate and product can be retained in cells by the aforementioned methods.

Retention of the substrate in the cell can be accomplished either by, as described above, an increase in polarity or binding to cellular constituents, or the cells can be put into "second conditions." Under the second conditions, the cells are brought to a lower temperature, below about the membrane freezing temperature, generally 0°-15° C. preferably 4° C. Thus, due to the polarity of the enzyme product and/or the second conditions, leakage of substrate from the cells can be minimized and the substrate may be maintained in the cells for the period of the assay. A less polar product may leak from the cells. This leakage is substantially diminished by the presence of polar substituents on the fluorogenic compound. A further reduction may be achieved by reducing the temperature to below about 15° C., usually below about 10° C., and usually not lower than about 0° C., whereby any leakage is further diminished.

There is an endogenous $\beta$-galactosidase in some mammalian cells, for example macrophages and those becoming confluent in culture. The presence of the endogenous $\beta$-galactosidase may be accounted for in a variety of ways. Simply, cells which do not contain the expression construct may be used as controls and the values observed with these cells subtracted from the values obtained with cells which do have the construct.

Alternatively, selective inhibitors may be employed, which selectively inhibit the endogenous enzyme as distinct from the enzyme encoded by the expression construct. For example, in the case of β-galactosidase, the endogenous enzyme is found in lysosomes and can be inhibited by incubation with chloroquine, or 5% DMSO, so as to substantially reduce the background value. (DeGroot et al., *Experimental Cell Research* (1981) 136:327-333.)

In order to provide for modulation of the enzyme activity as well as to extend the dynamic range an enzyme inhibitor, particularly a competitive enzyme inhibitor, may be employed so that a reasonable time period for the linear rate of fluorescein product production may be obtained. A number of inhibitors, both reversible and irreversible, exist for β-galactosidase, for example mercuric ion or phenylethylthio-β-galactoside, respectively. The amount of the inhibitor will be determined by the efficiency of transfer of the inhibitor across the membrane, the $K_i$ of the inhibitor, the enzyme activity in the cell, and the like. Therefore, the concentration of inhibitor in the external medium will vary widely and will usually be determined empirically. In many situations, a convenient concentration has fallen between 0.1 and 10 mM. Conveniently, the inhibitor and the substrate are combined in the same medium for transport across the membrane into the host cell at the same time.

The cells are then allowed to incubate for sufficient time at the reduced temperature, so as to have a sufficient turnover of substrate to produce a detectable signal. The signal may be observed in a variety of ways. Aliquots may be taken and used for fluorescence activated cell sorting (FACS), flow cytofluorometry or static cytofluorometry in a microscope or similar static device. In this manner, a distribution will be obtained for the various levels of fluorescence in the various cells, where the population acts in a heterogeneous manner. The total number of fluorescent cells may be determined where only a fraction of the total cells are infected to provide a particle count. Alternatively, or in combination, total fluorescence may be integrated at different times, so that an overall value may be obtained and the rate of change of the total fluorescence in the cells determined. The background value may be subtracted by employing controls, so that the increase in number of fluorescent cells and fluorescence per cell over time of the cell population may be determined and related to the factor of interest. Alternatively, the cells may be spread on a slide and a fluorescence microscope with an associated fluorometer employed to determine the level of fluorescence of individual cells or groups of cells. The particular manner in which fluorescence is determined for the cells in the assay is not critical to this invention and will vary depending upon available equipment, the qualitative or quantitative nature of the assay, and the like.

The subject method may be employed for the detection of a large number of viruses of interest. Viruses which may be assayed include HIV, HTLV-I, -II hepatitis virus, such as B, non-A, non-B, FeLV, FSC, etc. Other viruses of interest include Epstein-Barr virus, Herpes simplex virus I and II, cytomegalovirus, etc. Sodroski et al., *Science* (1984) 225:381-385: Nabel et al., *Science* (1988) 239:1299-1301: Jameel et al., *Mol. and Cell. Biol.*, Feb. 1986, 710-715: O'Hare and Goding, *Cell* (1988) 52:435-455: Preston et al., *Cell* (1988) 52:425-434: Takada et al., *J. Virol.*, Mar. 1986, 1016-1022: Koszinowski et al., *J. Virol.*, Apr. 1986, 59-66.

The subject method may also be used to investigate the effect of compounds on replication and maturation of virus particles. By employing an infected host cell having a subject construct containing a transcriptional element modulated by a viral product, the fluorescent level of the cell will be an indication of the level of expression of such viral products. A change in fluorescent level as a result of the presence of a particular compound may be associated with the effect of such compound on the ability of the virus to replicate and/or mature to an infectious virion.

The expression construct may be introduced into the host cell by any convenient means. By employing a virus, the host cell may be transfected so as to provide for integration. In some instances, the replication system of a virus may be employed to provide for episomal elements. In this situation, it will usually be desirable to provide for a marker, so that selection may be maintained to ensure the stable maintenance of the episomal elements.

A kit may be provided for the subject method, which would comprise a combination of the substrate and competitive inhibitor in conjunction with the construct in a form for introduction into a mammalian host cell. Alternatively, transformed host cells containing the construct may be included as part of a kit.

The following examples are offered by way of illustration and not by way of limitation.

EXPERIMENTAL

Materials and Methods

Cells and Tissue Culture. NIH 3T3 cells were obtained from M. Dieckmann and P. Berg (Stanford University). The cell lines ψ-2-MMuLVSVnlsLacZ (ψ-2-21C) and ψE-34 (Sanes et al., *EMBO J.* (1986) 5:3133-3142) were derived by recombinant retroviral infection of ψ-2 (Mann et al., *Cell* (1983) 3:153-159) and maintained as described (Bonnerot et al., *Proc. Natl. Acad. Sci. U.S.A.* (1987) 84:6795-6799. The T-cell line BW5147 and the SP2/0 B hybridoma were maintained in complete RPMI 1640 medium (10% added fetal calf serum) at 5% $CO_2$/95% air.

Retroviral Infections. Retrovirus producer cells ψ-2-21C were plated to a density of $10^6$ cells per 100 mm plate in 7 ml of fresh Dulbecco's modified Eagle's medium. After 24 hr. 6 ml of virus-containing medium was filter-sterilized, and Polybrene was added to 10 μg/ml. Virus (3 ml) was added to $10^6$ cells in 3 ml of RPMI 1640 medium. After 4 hr. cells were washed and replated.

Chemicals. FDG (fluorescein digalactopyranoside was supplied by R. Haugland (Molecular Probes, Eugene, Oreg.: catalog no. 1179). Contaminating fluorescent fluorescein mono-β-D-galactopyranoside, which develops during dry storage, was bleached with 488 nm light from an argon laser. X-Gal and orthonitrophenyl-galactoside (ONPG) were obtained from Boehringer Mannheim.

Fluorescence Activated Cell Sorting (FACS) and Analysis. FACS was set up as described (Parks et al., (1986) in *The Handbook of Experimental Immunology*, eds. Weir et al., (Blackwell, Edinburgh) 4th ed, pp. 29.1-29.21). The autofluorescence of cultured cell lines was compensated for as described (Alberti et al., *Cytometry* (1986) 8:114-119). Multiparameter data were collected and analyzed by using FACS-DESK run on a Digital VAX-780 configured as described (Moore and Kautz, (1986) *The Handbook of Experimental Immunology*, eds. Weir et al., (Blackwell, Edinburgh) 4th ed, pp. 30.1-30.11). Fluorescence intensity of individual cells was measured as relative fluorescence unit(s) (FU).

X-Gal Staining. After 8 hr of X-Gal staining as described (Sanes et al., *EMBO J.* (1986) 5:3133-3142), blue cells were scored visually.

FDG Staining for β-Galactosidase. Exponentially growing fibroblast cells were treated with trypsin (GIBCO no. 610-5400: diluted to 1x solution) in phosphate-buffered saline until they could be removed from the plate with mild agitation. BW5147 and SP2/0 suspension cells in exponential phase were pelleted and resuspended in phosphate-buffered saline. Cells for staining were counted and brought to $10^7$ per ml in RPMI 1640-deficient medium (GIBCO no. 9826) containing 2% (vol/vol) fetal calf serum, 10 mM Hepes (pH 7.3), and 1 μM propidium iodide (incubation medium). The protocol for staining cells is as follows: (i) add 100 μl of cells at $10^7$ per ml to a 5 ml polystyrene tube: (ii) bring the cell suspension to 37° C. in a water bath for 5 min: (iii) add 100 μl of 2 mM FDG in $H_2O$, prewarmed to 37° C.; (iv) mix gently but thoroughly and rapidly place back into the 37° C. water bath for 1 min: and (v) place the tube on ice and add 1800 μl of ice-chilled isotonic incubation medium.

RESULTS

FDG Substrate Loading via Hypotonic Shock at 37° C. and Incubation at 4° C. Fluorescein passes the cell membrane >200 times faster at 37° C. than at 5° C. (Thomas et al., *Biochemistry* (1979) 181:2210-2218), whereas the $V_{max}$ of β-galactosidase is lowered by only a factor of about 10 over this temperature differential (Wallenfels and Melhotra (1960) *The Enzymes*, eds. Boyer et al., (Academic Press, N.Y.) 2nd ed.). Loading the substrate at high concentrations under hypotonic conditions at 37° C., with a subsequent rapid switch to cold temperature (thus allowing enzyme activity to proceed while preventing fluorescein or FDG leakage), affected the resolution of a mixture of LacZ+ and LacZ− cells. Therefore, cells were loaded in the presence of 1 mM FDG at 50% of isotonic salt concentration at 37° C. for 1 min. Cells were then rapidly cooled by 1:9 dilution with ice-cold isotonic medium and placed at 4° C. to allow fluorochrome generation. This procedure gave excellent generation and resolution of peaks. LacZ− cells did not develop any fluorescence above the autofluorescent background. After 60 min, LacZ+ cells generated a narrow peak of fluorescence with a minor "trailing" population of cells, whereas a mixture of equal numbers of LacZ+ and LacZ− cells stained together generated two discrete peaks. When incubation at 4° C. was extended beyond 60 min, the major peak did not move, but the trailing population gradually merged with the major peak, indicating that the major peak represents cells that contain sufficient enzyme to have hydrolyzed all intracellular FDG and the trailing population represents cells with much lower levels of β-galactosidase activity.

The two major populations stained were sorted by employing a sort rate of about 3000 cells per sec. Subsequent staining of these sorted populations with X-Gal for postmortem analysis of LacZ content showed sorting efficiencies that were theoretically expected (Parks et al. (1986) supra): percent positives from the positive sort=98.5%: percent negatives from the negative sort=>99%.

Excellent discrimination was also obtained of LacZ+ and LacZ− cells of other developmental lineages after infection with the recombinant LacZ retrovirus ψ-2-21C. $1 \times 10^6$ SP2/0 and BW5147 cells were infected with this retrovirus and, after waiting 3 days for integration of the retrovirus and expression of LacZ. the FACS-FDG assay was performed. Mock-infected control cells had low autofluorescence, between 0.1 and 1.0 FU. However, 4% of the infected BW5147 cells and 2% of the infected SP2/0 cells had fluorescence of 1.0–100 FU. To separate LacZ− from infected LacZ+ cells, cells were sorted with <1.0 FU (LacZ−) and >2.0 FU (LacZ+) from both BW5147 and SP2/0 populations. The sorted cells were immediately fixed and stained with X-Gal. The LacZ−-sorted populations did not contain any blue cells, whereas the LacZ+-sorted populations included cells that stained white, light blue, or dark blue. Thus, none of the cells defined as LacZ− by the FACS-FDG assay stain with X-Gal. However, only some cells defined as LacZ+ by the FACS-FDG assay stained blue with X-Gal.

Clones derived from these infected BW5147 populations had similar X-Gal staining phenotypes. In another experiment, ψ-2-21C-infected BW5147 and SP2/0 cells were again assayed by FACS-FDG, and those cells fluorescing >2.0 FU (after 1 hr of incubation) were cloned by using the single-cell deposition capability of the FACS (Parks et al. (1986) supra). After growing clones for 1 week, cytochemical staining with X-Gal revealed that 70 of 79 BW5147-21C clones selected by FACS for β-galactosidase activity display a wide range of percentages of blue cells: from <1% blue to >95% blue. Pictures of representative clones BW5147-21C.28 and BW5147-21C.42 stained with X-Gal were made. All 20 SP2/0-21C clones examined had only a small population of cells, <1%, that stained blue. Therefore, cells expressing LacZ can be viably cloned by FACS, but cells within the clones exhibit apparent variable expression. Efforts were made to understand the relationship between the intensity of blue staining with X-Gal and β-galactosidase activity as determined by FACS-FDG in the BW5147-21C clones.

Fluorescence Accumulation Within Cells Is Directly Proportional to β-Galactosidase Enzymatic Activity and Is a More Sensitive Indicator of LacZ Expression Than X-Gal. Although many cells within some LacZ+ BW5147-21C clones had no detectable β-galactosidase activity when assayed with the X-Gal histological stain, almost all of the cells within these clones expressed some β-galactosidase as determined by using the FACS-FDG assay. Histograms of fluorescence distribution per cell of representative clone BW5147-21C.28 at three time points after FDG loading were prepared. By 11 min. >90% of the cells in clone 28 were fluorescing more than the negative control population. X-Gal staining of clone 28 revealed only 23% of the cells that could be visually determined as blue, indicating FACS-FDG detects β-galactosidase activity in cells that X-Gal does not.

From these histograms the arithmetic mean fluorescence per cell was calculated. Plots of the mean fluorescences versus time for BW5147-21C.28 and several other BW5147-21C clones revealed that the fluorescence increase is clone-dependent, initially linear, and eventually plateaus. This plateau is due to substrate exhaustion and is a measure of the total amount of FDG actually taken up during loading.

The broad fluorescence profiles displayed within these clonal populations after 6 months of growth could reflect epigenetic variations in the level of expression of LacZ. To determine if this variable β-galactosidase activity is heritable and whether the amount of fluorescence within each cell is proportional to the enzyme activity, BW5147-21C.28 was subcloned using FACS. Gates were set to sort FDG-loaded cells having 0.1-1 FU per cell after 10 min of incubation at 4° C., with the expectation that these cells and their progeny would express low levels of LacZ activity. The β-galactosidase activity in the FACS-FDG assay of three representative subclones, the parental line, clone 28, and clone 42, was determined. As expected, each subclone generated fluorescence at a much lower rate than did the parental clone 28, while clone 42 maintained its high-activity phenotype. Cells ($5 \times 10^6$) of each clone and subclone were lysed, and the total β-galactosidase activity was determined by the chromometric ONPG assay. The rate of ONPG cleavage in the extract versus the mean rate of fluorescence increase in individual cells showed excellent correlation over a 200-fold range of β-galactosidase acivities, indicating that FACS-quantification of FDG cleavage is an accurate measurement of β-galactosidase content determined conventionally. Comparison of the respective time scales and numbers of cells analyzed indicated that the FACS-FDG assay is about 8 orders of magnitude more sensitive than the ONPG assay.

Whether the property of individual cells to stain blue with X-Gal was related to the FU intensity in the FACS-FDG assay was assessed. The percentage of blue X-Gal-stained cells within each clone was determined and used to calculate the threshold FU above which there was a corresponding percentage of cells in the respective histograms of FU per cell at 2 min. Table 1 shows that an average of these threshold values, 7.3 FU per cell at 2 min, provides a value that predicts the percentage of blue X-Gal-stained cells determined visually within each clone.

TABLE 1

Prediction of the Percentage of Blue Cells Using the Calculated Fluorescence Threshold

| Clone | % Blue Cells Observed | Threshold, FU | % Blue Cells Predicted |
|---|---|---|---|
| 42 | 93 | 4 | 87 |
| 28 | 23 | 8 | 25 |
| 28lo4 | 4 | 10 | 9 |
| 28lo2 | <1 | — | 0.87 |
| 28lo1 | <1 | — | 0.28 |

Columns from left to right: BW5147-21C clones and subclones used in this experiment; percentage of blue cells determined visually after staining with X-Gal; calculated fluorescence threshold in FU at 2 min, derived from respective fluorescence histograms for each clone, above which there is a percentage of cells corresponding to the percentage of blue cells in the preceding column; and the average of the three fluorescence thresholds applied in a regression analysis to predict the percentage of blue cells expected.

Following the procedures described above, during the osmotic shock, in separate experiments either 1 mM mercuric or 1 mM phenylethylthio-β-galactoside was included with FDG. In each case, a substantial reduction in the enzymatic activity of the cells was observed in that the time in which a particular fluorescence level was achieved was lengthened. Thus, by using competitive or non-competitive enzyme inhibitors it was shown that the turnover rate from FDG to fluorescein was substantially diminished approaching zero. In this way, the time for observation of a linear portion of the curve of change in fluorescent concentration could be extended, or the generation of fluorescence could be essentially stopped to allow later convenient measurement of fluorescence in many samples, to simplify the monitoring of the assay.

In carrying out the assay, rather than determining enzyme activity or a rate, employing two or more determinations, an endpoint assay can be carried out by terminating the enzyme reaction. This can be achieved by use of a chemical inhibitor, such as has been described for inhibition, at a concentration which terminates the reaction, a denaturing agent, such as heat, or the like. In this way, samples could be prepared in a multiplicity of wells, such as a microtiter plate, the cells co-cultivated with the sample suspected of containing infectious particles, followed by osmotic shock, incubation for sufficient time to provide a fluorescent signal, followed by termination of the enzyme reaction by any convenient means. The samples may then be assayed at leisure, since the amount of fluorescent agent should remain substantially constant.

pPAZ is a self-inactivating (SIN), defective Moloney retroviral vector containing the San Francisco isolate ARV Human Immunodeficiency Virus (HIV) long terminal repeat (LTR), and trans-activating region (tar), fused 5' proximal to the β-galactosidase (LacZ) structural gene of *E. coli*. It was constructed in the following manner:

1) The plasmid pCH110 (Hall et al., *J. Mol. Appl. Gen.* (1983) 2:101-109) was cut with HindIII and BamHI. The approximately 3.8 kilobase DNA fragment containing the LacZ structural gene and polyadenylation signals of SV40 was isolated (fragment 1).

2) The plasmid pHIVCAT (Kao et al., *Nature* (1987) 330:489-493) was also cut with HindIII and BamHI and the 3.0 kilobase DNA fragment containing the HIV LTR/tar, and pBR322 sequences necessary for cloning and maintenance of the plasmid in *E. coli* was isolated (fragment 2).

3) The intermediate construct pARV-Z was constructed as follows: Fragments 1 and 2 were ligated under standard conditions, transformed into *E. coli* by standard techniques, and plated onto ampicillin/X-Gal plates. After 24 hours of growth, blue colonies on X-Gal plates indicated the presence of LacZ gene activity. Subsequently, plasmid was isolated from test colonies and verified as the required intermediate construct pARV-Z by standard diagnostic techniques (in this case, recutting the test plasmids with BamHI and HindIII).

4) pARV-Z was cleaved with AhaIII and a 3.8 kilobase fragment containing the HIV LTR/tar fused to the LacZ structural gene was isolated (fragment 3). The self-inactivating Moloney murine leukemia virus construct pJrPro- was cleaved with XhoI and BamHI. (pJrPro- is freely obtained for LacZ experiments from the laboratory of Richard Mulligan MIT: an alternative example of a self-inactivating retrovirus construct is in Yee et al., *Proc. Natl. Acad. Sci. U.S.A.* (1987) 84:5197-5201.) The XhoI and BamHI ends were blunted by filling in the ends with the Klenow Fragment of DNA polymerase (fragment 4). Fragments 3 and 4 were ligated by standard procedures (as above), transformed into *E. coli*, plated onto ampicillin/X-Gal and blue colonies picked and assayed for correct orientation of the HIV-LacZ fragment in the pJrPro- vector.

The constructed vector was called pPAZ (plasmid Promoter minus ARV LTR LacZ).

5) pPAZ was co-transfected with pSVtat (to prevent premature termination of the retroviral transcript) and pSV2neo (to select cells competent for DNA uptake) by electroporation into the defective amphotrophic retrovirus helper line PA317 (Miller et al., *Mol. and Cell. Biol.* (1986) 6:2895–2902). Transfectants were selected in G418. Colonies are screened for virus production by infecting a constructed NIH3T3-derived cell line transfected with pSVtat, and staining for LacZ activity by FACS-FDG and X-Gal. High titer virus are used to infect the cell line H9 or Jurkat. Clones with an integrated pPAZ retrovirus are screened and selected by FACS-FDG based on their ability to be transiently trans-activated by transient transfection and expression of pSVtat. The appropriate target cell clone for detection of infectious HIV particles is a clone showing very low or no basal expression of LacZ from the HIV LTR/tar promoter. The said target cell clone upon infection by HIV is trans-activated to produce β-galactosidase which can be readily measured in the aforementioned assay systems.

Cells containing the subject construct are co-cultivated for two days with blood from the patient whose blood is being assayed. At the end of the two days, the cells are isolated, washed and analyzed by FACS or flow cytofluorimetry. The number of fluorescent cells and level of fluorescence is used to quantitate the number of infectious HIV particles in the blood sample. The quantitation is achieved by preparing standards from samples having known numbers of HIV particles and carrying out the same assay, whereby the results obtained with the samples are compared with the standards.

It is evident from the above results that a sensitive technique is provided for evaluating transcriptional initiation regulatory regions in a viable cell host, so that the observed results may be accurately compared to the normal environment in the cell. In this manner, a more accurate understanding of a variety of cellular processes may be determined, the utilization of various functional sequences evaluated and compared, and the utility of functional sequences standardized. In addition, functional sequences may be analyzed as to those portions which are essential and those portions which may affect function but are not essential to activity. The method also allows for the detection of trans-activating entities, which allows for the detection of the presence of any pathogen which can affect a cell host and produce a transacting product which results in a change in the level of transcription or translation. Therefore, viruses which produce a transacting regulatory element may be quantitated by co-cultivation of host cells with a sample suspected of containing infectious virus particles. The method is fairly rapid, highly sensitive and can provide for accurate results as to the state of infection of an individual, as distinct from a past condition, which can be the result with an assay for antibodies.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for studying a regulatory element of a transcriptional initiation regulatory system in a viable mammalian cell, said cell comprising a non-wild type expression construct comprising a transcriptional initiation regulatory region comprising a regulatory sequence of interest and a structural gene encoding β-galactosidase, wherein said β-galactosidase employs as a substrate a β-galactosidyl ether of a fluorescent phenolic compound that produces a fluorescent product upon hydrolysis of said ether, said method comprising:

substantially irreversibly introducing said substrate into said cell in a hypotonic solution at a temperature in the range of about 25°–40° C.;

incubating said cell at a temperature below about the membrane freezing point; and detecting said fluorescent product in said cell as a measure of the activity of said regulatory element.

2. A method according to claim 1, wherein said element is a trans acting element.

3. A method according to claim 1, wherein said element is a cis acting element.

4. A method according to claim 1, wherein said detecting is with a fluorescence activated cell sorter.

5. A method according to claim 1, wherein a competitive enzyme inhibitor is in said cell during said incubating.

6. A method for producing a fluorescent product in a viable mammalian cell, said cell comprising a non-wild type expression construct encoding the enzyme β-galactosidase, said method comprising:

substantially irreversibly introducing under a first set of conditions fluorescein di-β-galactopyranoside or derivative thereof as the enzyme substrate into said cell, wherein said substrate is characterized by being capable of substantially irreversible introduction into said viable cell and produces a product which is substantially retained in said cell under the conditions of producing said fluorescent product;

incubating said cell under a second set of conditions at a lower temperature than said first set of conditions, where said fluorescent product is produced;

wherein said first set of conditions comprises a hypotonic solution and a temperature in the range of about 25°–40° C. and said second set of conditions comprises a temperature below about the membrane freezing point; and detecting said fluorescent product in said cell.

7. A method according to claim 6, wherein phenylethylthio-β-galactopyranoside is introduced into said cell with said substrate in an amount sufficient to reduce the endogenous enzyme activity.

8. A method for detecting the presence of an infectious virus in a sample, said method employing a test viable cell susceptible to said virus and comprising a non-wild type expression construct comprising a transcriptional initiation regulatory region including a regulatory sequence which is responsive to a trans acting entity produced by said virus and a structural gene encoding β-galactosidase under the transcriptional initiation regulation of said regulatory region, said method comprising:

cultivating said test viable cell with said sample under conditions wherein said test viable cell becomes infected with any infectious virus present in said sample;

substantially irreversibly introducing into said cell as the enzyme substrate fluorescein di-β-galactopyranoside or derivative thereof by means of a hypotonic solution of said substrate at a temperature in the range of about 25°–40° C. for a time sufficient to introduce an excess of substrate and minimize reaction of said substrate and then cooling said cell to a temperature below about the membrane freezing point;

incubating said cell for a sufficient time for said fluorescent product to form; and detecting said fluorescent product as a measure of the presence of said infectious virus in said sample.

9. A method according to claim 8, wherein said infectious virus is HIV and said regulatory sequence is the tar sequence.

10. A method according to claim 8, wherein said hypotonic solution further comprises the irreversible enzyme inhibitor mercuric ion or competitive inhibitor phenylethylthio-β-galactopyranoside.

11. A method according to claim 8, wherein said detecting is by means of a fluorescent activated cell sorter or flow cytometer.

12. A method according to claim 8, wherein said detecting is by means of a fluorometer or fluorescence microscope.

13. A method according to claim 8, wherein said cell is a CD4+ cell.

* * * * *

UNITED STATES PATENT AND TRADEMARK OFFICE
CERTIFICATE OF CORRECTION

PATENT NO. : 5,070,012
DATED : December 3, 1991
INVENTOR(S) : Garry P. Nolan; Steven Fiering; Leonard A. Herzenberg It is certified that error appears in the above-identified patent and that said Letters Patent is hereby corrected as shown below:

Column 1, line 4, insert:

--This invention was made with Government support under PHS Grant No. 5-R35-CA42509-02. The Government has certain rights in this invention.--

Signed and Sealed this

Sixth Day of December, 1994

Attest:

BRUCE LEHMAN

Attesting Officer

Commissioner of Patents and Trademarks